United States Patent
Shin

(10) Patent No.: US 6,921,372 B2
(45) Date of Patent: Jul. 26, 2005

(54) PORTABLE ACUPRESSURE THERAPEUTIC TREATMENT DEVICE

(76) Inventor: Derek Shin, 1020 McNicoll Avenue, #144, Scarborough, Ontario (CA), M1W 2J6

( * ) Notice: Subject to any disclaimer, the term of this patent is extended or adjusted under 35 U.S.C. 154(b) by 359 days.

(21) Appl. No.: 10/349,523

(22) Filed: Jan. 24, 2003

(65) Prior Publication Data

US 2004/0147959 A1 Jul. 29, 2004

(51) Int. Cl.[7] .............................. A61F 5/00; A61H 39/00
(52) U.S. Cl. ....................... 601/134; 601/136; 606/204; 5/632; 5/630
(58) Field of Search ........................... 601/28, 112, 113, 601/115, 128, 134, 135, 136, 137, 138, 148; 606/201, 204, 240; 607/148; 482/140, 142; 128/845; 5/630, 632, 633, 676, 652, 944

(56) References Cited

U.S. PATENT DOCUMENTS

| | | | | |
|---|---|---|---|---|
| 3,705,579 A | * | 12/1972 | Morini et al. ................ | 601/121 |
| 4,974,582 A | * | 12/1990 | Johnson ........................ | 601/134 |
| 5,433,689 A | * | 7/1995 | Frins ............................ | 482/142 |
| 5,820,573 A | * | 10/1998 | Ramos ......................... | 601/134 |
| 5,913,839 A | * | 6/1999 | Wincek ....................... | 601/134 |
| 5,938,684 A | * | 8/1999 | Lynch et al. ................. | 606/204 |
| 6,305,040 B1 | * | 10/2001 | Myler ............................ | 5/636 |

* cited by examiner

Primary Examiner—Danton D. DeMilie
Assistant Examiner—Quang D. Thanh
(74) Attorney, Agent, or Firm—David W. Wong

(57) ABSTRACT

A therapeutic acupressure device has a mat with a top surface shaped to conform to the back contour of a person lying on it in a supine position. Two elongated spaced mutually parallel fuzzy fabric strips are provided at the center of the mat. The mat has a transverse rounded hump to support the lordotic curve of the lumbar spine. A cervical support is adjustably positioned on the mat to support the person's neck portion. A plurality of resilient twin spherical acupressure balls of various hardnesses are placeable at selected positions on the fuzzy fabric strips to provide desired therapeutic treatment for the person. A grid is marked beside the sides of the fuzzy fabric strips to guide the placement of the acupressure balls.

13 Claims, 4 Drawing Sheets

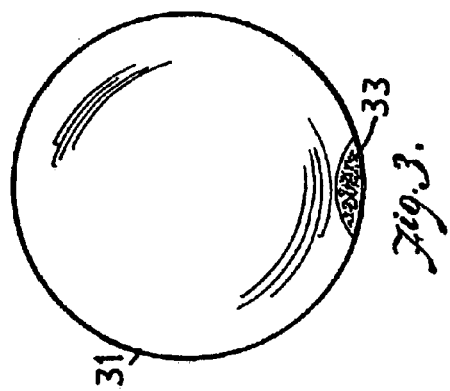
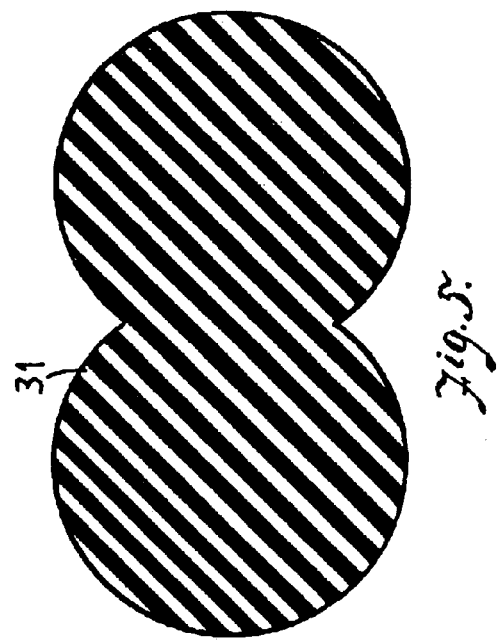
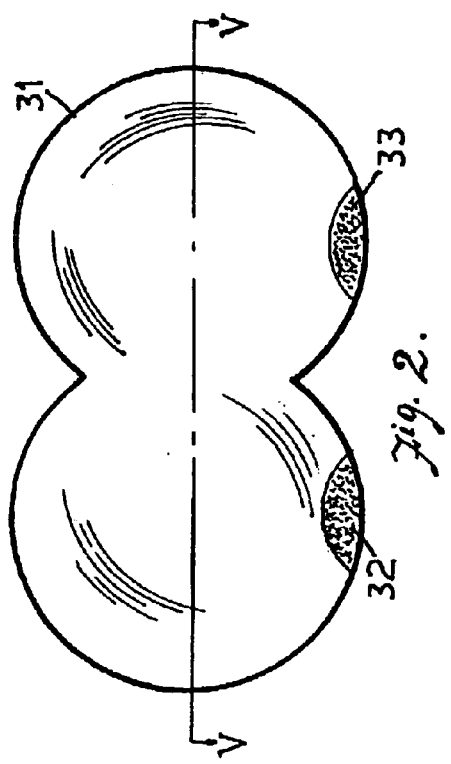
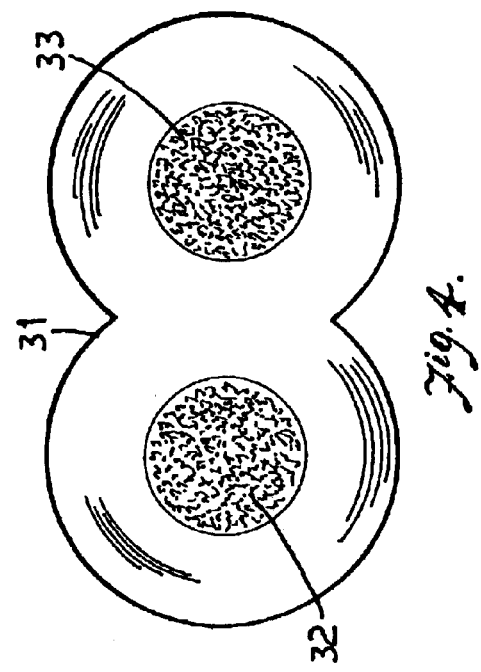

PORTABLE ACUPRESSURE THERAPEUTIC TREATMENT DEVICE

FIELD OF INVENTION

This invention relates to an acupressure treatment device and more particularly relates to a portable device for providing therapeutic treatment in selected degrees of stationary or dynamic acupressure in associate points of the human body.

BACKGROUND OF THE INVENTION

In the Eastern philosophy of shiatsu and acupressure it is believed that a life energy, called "chi" flows through the entire human body in specific channels or "meridians". Along each meridian there are specific points which when stimulated by a right amount of external pressure, will elicit specific therapeutic responses. One of the most important meridians in the body is the bladder meridian which flows down the length of the spine at one and a half Chinese inch or "chun" from along its two sides. One Chinese chun is equal to about one and half inch long. The bladder meridian is important because it consists of a number of acupressure points called "associate points" which correspond to different organs and energy points in the body; therefore, one can elicit therapeutic effects in the whole body by invoking or stimulating these associate points. All associate points located at specific locations are designated by shiatsu numbers. For example, the bladder point No. 15 is located at 14 chuns above the tail bone. When this bladder point is stimulated it will invoke the heart meridian resulting in decreased feelings of stress and anxiety. The associate points are also important because they locate along the length of the paraspinal muscles which are often hypertonic and full of myofascial trigger points due to undo stress caused by postural forces and overuse. These trigger points can cause local and referred pain throughout the back, neck, buttocks, legs, shoulders, arms, chest, abdomen and head. Pressure massage, longitudinal muscle stripping, and cross fiber frictions are the most effective massage techniques to release these trigger points. Pressure massage is the application of a downward localized force at a selected point of the muscle. Longitudinal muscle stripping is the action of exerting a downward kneading force along the longitudinal direction lengthwise along the muscle. Cross fiber friction is the action of applying a downward grinding force transverse to the longitudinal direction of the muscle.

Acupressure may be applied to associate points by using a handheld device which is operative for applying a localized pressure at a selected associate point, one at a time. Multiple acupressure may be applied to several associate points simultaneously by lying on a bed or table having upwardly protruding objects fixedly mounted at various predetermined locations thereon such that when a person lies in a supine position on the bed the weight of the person's body will cause the objects to apply acupressure at these predetermined locations of the body to provide the desired therapeutic treatments. A muscle massager is shown in U.S. Pat. No. 3,756,224 to R. D. Layman, which consists of several rows of rotary wheels mounted within a frame. When a person lies on the device in a supine position the wheels would exert a massaging action along the longitudinal direction to a person's back muscles to provide general release to muscle tensions. However, the device does not allow the user to select the position of the rollers in order to apply the acupressure at selected associate points of the body for specific desired therapeutic treatment as mentioned above. Also, since the wheels are recessed into the frame, their size is limited by the height of the frame so that only limited amount of pressure can be exerted on the muscle by the wheels.

U.S. Pat. No. 5,820,573 to G. M. Ramos shows another massage device which consists of a bed having a top surface shaped to conform generally with a person's back contour. A plurality of upstanding rigid cylindrical elements referred to as nibs are mounted fixedly at selected locations on the bed. The nibs have different height such that their tips form a curvature conforming to the back curvature of the person's back. When the person lies onto the nibs, they provide acupressure to the person's back muscle in various areas. The device is intended to provide only static pressure or non-dynamic massage on a person's overall back muscles to relieve any tension in the muscles per se. It does not provide acupressure to specific associate points according to the shiatsu and acupressure principle. The rigid nibs cannot provide rolling pressure on the muscles along their longitudinal and transverse directions. Such longitudinal motion is essential to provide longitudinal stripping of the muscles in muscle therapy in order to stretch and lengthen muscle fibers and to reduces muscle spasm, as well as to push out metabolites and waste products such that new blood may enter the muscle cells so as to reduce pain. Also, the rigid nibs cannot provide a massage action to the muscles in a direction that is transverse to their longitudinal direction. Such cross fiber frictions are effective for the breakdown of any scar tissue and adhesions in the muscles that can compromise their strength and function to create pain, stiffness, and increased susceptibility to injury. Furthermore, it is time consuming to arrange the nibs of various lengths in order that the tips of the nibs form a curvature that conforms to the person's back contour. It is even more problematic when the nibs have to be re-arranged for the device to be used by persons of different heights. The necessity of having to arrange the plurality of nibs of various heights increases the margin of error in achieving a proper desirable contour.

U.S. Pat. No. 5,913,839 to C. P. Wincek shows another massaging board having a plurality of rubber balls fixedly mounted on a contoured board such that a person may lie thereon to massage the back muscles by the balls. The positions of the balls are permanently mounted at all the positions such that they may not be changed for providing proper back muscle massage for persons of different heights and for selecting desirable massage areas.

SUMMARY OF THE INVENTION

It is a principal object of the present invention to provide a device which is operative to provide acupressure to selected specific associate points of a person's body according to the shiatsu principle.

It is another object of the present invention to provide a device which facilitates the application of longitudinal stripping and cross fiber frictions as well as kneading massage to a person's paraspinal muscles.

It is another object of the present invention to provide a device having acupressure balls of various hardnesses such that the user may customize the exact treatment intensity for each specific target area.

It is yet another object of the present invention to provide a device which is easy to set up and to readjust for treating users of different heights.

It is still another object of the present invention to provide a device which may operate to provide a deep intensity to target areas of a person's back muscles.

BRIEF DESCRIPTION OF THE DRAWINGS

Other objects and advantages of the present invention will become apparent from the following detailed description of the preferred embodiments thereof in connection with the accompanying drawings, in which

FIG. 2 is a side elevation view of the twin spherical acupressure ball of the device of the present invention.

FIG. 3 is an end elevation view of the twin spherical acupressure ball of the device.

FIG. 4 is a bottom elevation view of the acupressure ball.

FIG. 5 is a cross section view of the acupressure ball along cross section line V—V of FIG. 2.

DETAILED DESCRIPTION OF THE PREFERRED EMBODIMENTS

Figure 1:
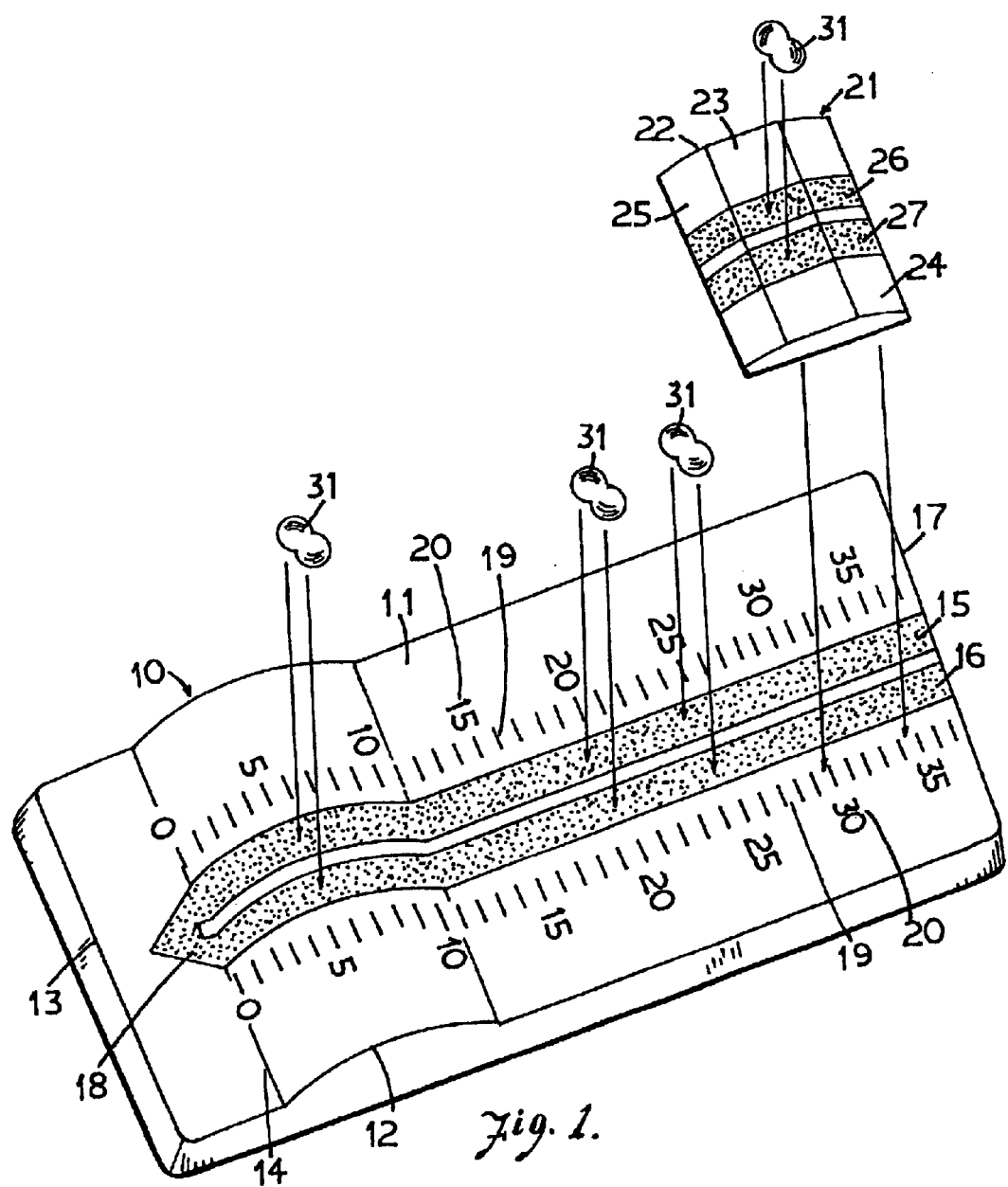
FIG. 1 is an exploded perspective elevation view showing the component parts of the device according to the present invention.
Figure 6:
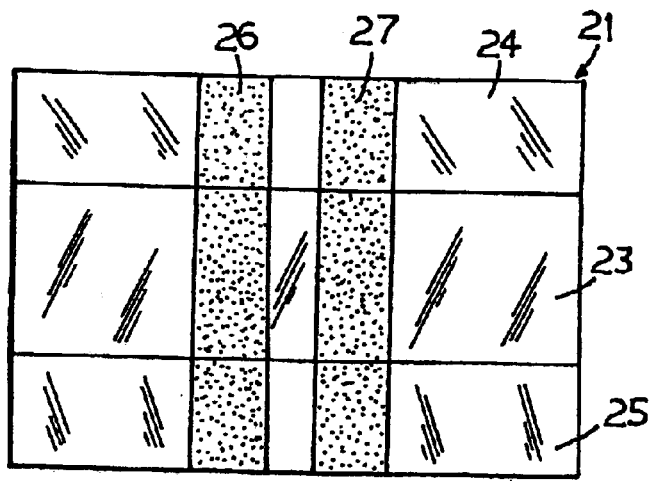
FIG. 6 is a top elevation view of the cervical support of the device according to the present invention.
Figure 7:
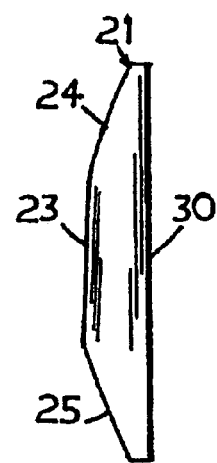
FIG. 7 is a side elevation view of the cervical support.
Figure 8:
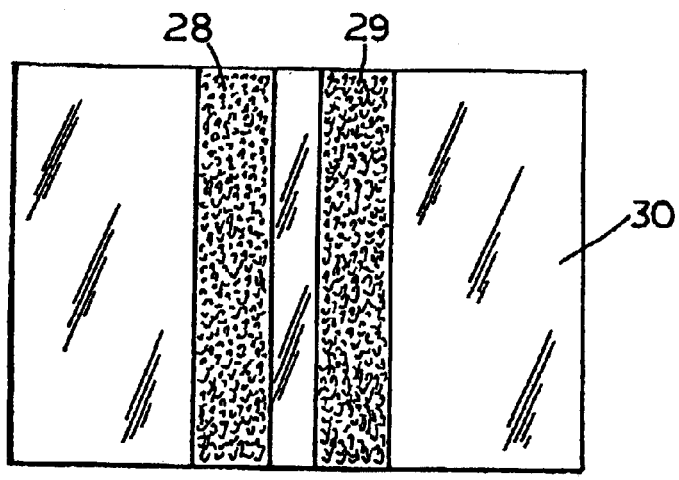
FIG. 8 is a bottom elevation of the cervical support.
Figure 9:
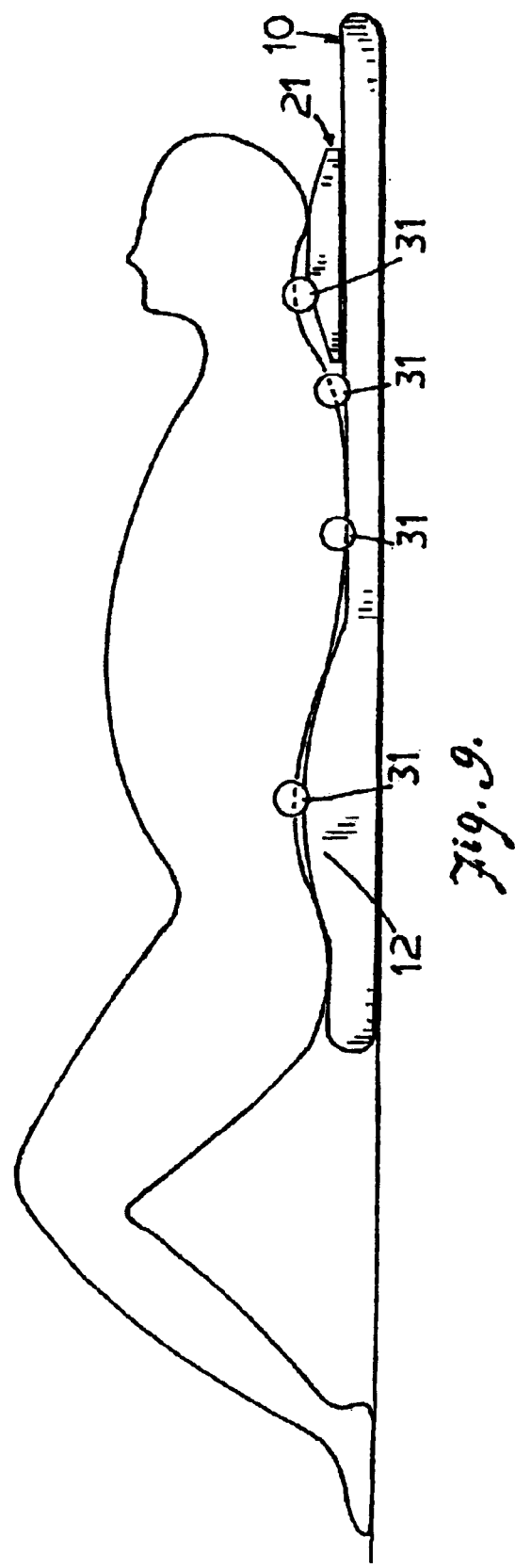
FIG. 9 is a side elevation view depicting the set up of the device during operation by a user.

With reference to the drawings wherein like reference numerals designate corresponding parts in the several views, the therapeutic device 10 of the present invention has a generally rectangular mat 11 which may be made of a resilient material such as dense foam or other suitable material such as rubber, styrofoam, natural or synthetic fibers, or wood. The mat 11 may be provided with a cloth or cloth-like outer cover which may be conveniently removed for cleaning purposes. The mat 11 has a typical overall longitudinal length of, for example, about 4 to 5 feet and 2 to 2.5 feet in width. A transverse arcuate hump 12 about 7 inches long is formed adjacent to the lower edge 13 of the mat 11. The arcuate hump 12 is about 5 inches in height and its lower edge 14 is spaced about 5 inches from the lower edge 13 of the mat 11. The hump 12 acts as a lumbar support such that when a person lies on the mat 11 the hump 12 would fit into the contour of the lordotic curve of the person's lumbar spine. Two spaced mutually parallel elongated strips 15 and 16 of fuzzy material or fabric such as the soft fuzzy half of a velcro (a trade mark) strip are provided at the middle portion of the mat 11 and they extend longitudinally from the lower edge 14 to the top edge 17 of the mat 11. The fuzzy strips 15 and 16 may be approximately 2 inches wide and each one is spaced about ½ inch from the longitudinal center line of the mat 11. The positions of the fuzzy strips 15 and 16 will align with the paraspinal muscle of a person lying on the mat. The lower ends of the fuzzy strips 15 and 16 is marked by a triangular pattern 18 which may be formed by an extension portion of the fuzzy strips 15 and 16. The triangular pattern 18 points downwards away from the lower end of the fuzzy strips 15 and 16, and it marks the position at which a person should locate the tail bone for lying properly on the mat during treatment.

A grid 19 is provided beside the two sides of the fuzzy strips 15 and 16. The grid 19 has numerical markings 20 which correspond to the designated numbers of the associate points of the person's meridian as described above.

The device 10 is provided with an adjustable cervical support 21 which may be rectangular in shape and having a top surface 22 consisting of a middle flat top portion 23 and a downwardly sloping upper edge portion 24 and a downwardly sloping lower edge portion 25. The cervical support 21 may be made of the same material as the mat 11 and is also provided with the same type of outer cover. Two spaced mutually parallel longitudinal fuzzy strips 26 and 27, similar to the fuzzy strips 15 and 16 on the mat 11, are provided on the top surface 22 of the cervical support 21 and they extend over the entire longitudinal length of the cervical support 21. Two parallel velcro(trade mark) clinging strips 28 and 29 are provided at the flat bottom surface 30 of the cervical support. The clinging strips 28 and 29 have a plurality of clinging bristles. The position and size of the clinging strips 28 and 29 are identical to that of the fuzzy strips 15 and 16 of the mat 11.

A plurality of semi-resilient twin spherical acupressure balls 31 are provided. For simplicity of illustration, four acupressure balls 31 are shown in the drawings. Each twin spherical acupressure ball 31 is shaped like two round balls joined together and it may be provided with a cloth-like outer cover. The acupressure balls 31 may be made of semi-resilient foam rubber or similar material and have various densities to provide a variety of hardnesses; and acupressure balls of different hardnesses have different colors for easy identification and selection. The twin spherical acupressure ball may be made by joining two round balls together or formed by integrally molding the material to the desired twin spherical shape. Clinging patches 32 and 33 such as the clinging half of a velcro (trade mark) material having a plurality of clinging bristles are provided at the two round bottom portions of the acupressure balls such that the acupressure balls 31 may be located safely at selected positions on the fuzzy strips 15 and 16 of the mat 11 and on the fuzzy strips 26 and 27 of the cervical support 21 by the interaction between the velcro (trade mark) clinging patches and the fuzzy strips; and yet the acupressure balls may sway sideway when subjected to external pushing forces.

The therapeutic treatment device 10 of the present invention may be set up by first placing the mat 11 on a hard flat surface. The user may then lie down in a supine position on the mat 11 by positioning the tail bone on the triangular pattern 18 located at the bottom edge portion of the mat. The cervical support 21 may then be positioned by placing it under the neck and head to conform to the natural curve of the neck. After the position of the cervical support 21 has been established, the cervical support 21 may then be fixed in place by the interaction 5 between the clinging strips 28 and 29 at the bottom of the cervical support with the fuzzy strips 15 and 16 respectively on the mat 11. The user may then get off the mat 11 and places a desired number of twin spherical acupressure balls 31 on the mat 11 straddling the fuzzy strips 15 and 16 such that the acupressure balls 31 are retained in place by the interaction between the clinging patches 32 and 33 of the acupressure balls 31 and the fuzzy strips 15 and 16 respectively. The exact locations of the acupressure balls 31 are determined by reference to the instructions manual which outlines the specific treatment protocols. The numerical markings 20 of the grid 19 facilitate the user to locate the acupressure balls readily corresponding to the instructions manual. The amount of acupressure balls used depends on the desired effect. Increasing the number of balls, for instance, would decrease the intensity of the pressure felt, and vice versa. Acupressure balls 31 of different hardnesses may also be selected and located at the different positions for providing the desired treatment. The color identification of the acupressure balls for indicating their hardnesses facilitates their selection.

After the acupressure balls 31 have been positioned, the user may then first sit down on the mat 11 with the tail bone located at the triangular pattern 18 and then slowly lying down with the acupressure balls 31 slowly exerting acupressure to the selected associate points of the paraspinal muscle due to the person's body weight. The user may stay stationary and let the body sink into the acupressure balls to produce a deep pressure point stimulation which stimulates the "A beta" sensory fibers thereby blocking the "pain gate" and reducing the sensation of pain. The full size of the acupressure balls 31 extending upwards from the mat 11 facilitates a deep pressure to be exerted at the selected associate points. This type of stimulus also contributes to the release of the body's natural opiates, such as endorphins and enkephalins that have a pain reduction and muscles relaxation effect. Pressure point stimulation also balances energy in the associated meridian which results in a decrease in pain, muscle spasm, and stress, and an increase in energy and feelings of relaxation.

For a dynamic massage, the user can achieve three different effects: Firstly, by moving the body in an up and down motion along the longitudinal direction of the mat 11. The acupressure balls 31 will sway up and down to provide a kneading action to the user's paraspinal muscles to create the longitudinal stripping of these muscles. Longitudinal stripping stretches and lengthens the muscle fibers, reduces muscle spasm, pushes out metabolites and waste products thus allowing fresh blood to enter the cells of the muscles to result in the reduction of pain. The swayable acupressure balls facilitate the application of a constant deep pressure in the muscles, that is moved through the tissue along the same direction of the muscle fibers. Secondly, by moving the body in a circular motion, the acupressure balls will also sway in a circular motion to create a circular kneading massage which is most effective for reducing muscle tension and increasing local circulation. Thirdly, by moving the body side to side, the acupressure balls will sway across the fibers of the paraspinal muscles to create cross fiber frictions which are effective for breakdown of scar tissue and adhesions in the muscle that can compromise the strength and function of the muscle creating pain, stiffness, and increased susceptibility to injury.

The mat 11 may be placed over the seat and backrest portion of a chair; and fasteners are provided for attaching it to the latter. The acupressure balls may then be placed on the fuzzy strips located on the backrest portion such that a person may sit on the chair and may then lean backwards on the acupressure balls to massage the back muscles.

Obviously, numerous modifications and variations of the present invention are possible in light of the above teachings. It is therefore to be understood that within the scope of the appended claims, the invention may be practiced otherwise than as specifically described herein.

What is claimed is:

1. A therapeutic acupressure device comprising,
    a mat adapted for a person to lie in a supine position thereon, said mat having an convex hump located at a lower edge portion therein, said hump being adapted to serve as a lumbar support of a lordotic curve of said person,
    two spaced mutually parallel elongated fuzzy strips located along two sides of a longitudinal center line of a top surface of said mat, said fuzzy strips extending from a top edge of said mat to a lower edge of said hump,
    a grid marking provided on said top surface and located beside two sides of said elongated fuzzy strips, said marking being indicative of associate points along paraspinal muscles of said person lying on said mat,
    a cervical support adjustably disposed on said mat and adapted to support a neck portion of said person lying on said mat, said cervical support having two spaced mutually parallel fuzzy strips similar to said fuzzy strips on said mat and extending from a bottom edge to a top edge therein,
    a plurality of twin spherical acupressure balls selectively located at desired positions on said fuzzy strips of said mat and said cervical support.

2. A therapeutic acupressure device according to claim 1 including a downwardly pointing triangular shape extension of said fuzzy strips located on said top surface of said mat and extending downward from said lower edge of said hump, said triangular shape extension adapted to indicate a location for said person to locate a tail bone body portion for lying properly on said mat during the therapeutic treatment.

3. A therapeutic acupressure device according to claim 2 wherein said mat is made of a material chosen from the group consisting of dense foam, rubber, styrofoam, wood and resilient material.

4. A therapeutic acupressure device according to claim 3 including two spaced elongated mutually parallel clinging strips provided at a bottom surface of said cervical support, said clinging strips having a plurality of clinging brittles cooperative with said fuzzy strips for retaining said cervical support at a selected location on said mat.

5. A therapeutic acupressure device according to claim 4 including clinging patches provided at a bottom surface of said twin spherical acupressure balls, said clinging patches being cooperative with said fuzzy strips on said mat and said cervical support for retaining said acupressure balls at said desired positions.

6. A therapeutic acupressure device according to claim 5 wherein said twin spherical acupressure balls are made of a semi-resilient material.

7. A therapeutic acupressure device according to claim 6 wherein said twin spherical acupressure balls have a variety hardnesses whereby acupressure balls of different hardnesses are selectively placeable at selected positions on said fuzzy strips to provide various desired therapeutic treatments.

8. A therapeutic acupressure device according to claim 7 wherein said acupressure balls of different hardnesses have different colors for easy identification and selection for obtaining the desired therapeutic treatment.

9. A therapeutic acupressure device comprising,
    a generally rectangular mat adapted for a person to lie thereon in a supine position to receive therapeutic treatment,
    a rounded hump formed adjacent to a bottom edge of said mat, said hump extending transversely across the entire width of said mat and being adapted to support a lumbar portion of said person during treatment,
    two elongated spaced mutually parallel fuzzy fabric strips provided on a top surface of said mat, said fuzzy fabric strips extending equal distance along both sides of a longitudinal center line of said mat from a top edge of said mat to a bottom edge of said rounded hump,
    a grid marking provided on said mat and positioned spaced from and beside side edges of said fuzzy fabric strips, said marking being indicative of locations of associate points of said person's paraspinal muscle,
    a triangular shape fuzzy fabric element formed on a bottom portion of said top surface of said mat and extending downwardly from said bottom edge of said rounded hump and pointing downward from said fuzzy fabric strips, a cervical support disposed adjustably at a selected position in a top portion said mat and being adapted to provide support for a neck portion of said person, said cervical support having two elongated fuzzy fabric strips similar to said fuzzy fabric strips of said mat and extending over the entire longitudinal length of a top surface of said cervical support, a plurality of resilient twin spherical acupressure balls placeable at selected positions on said fuzzy fabric strips of said mat and said cervical support, said acupressure balls having clinging patches provided on a bottom portion of each sphere therein, said clinging patches being cooperative with said fuzzy fabric strips for retaining said acupressure balls securely at said selected positions.

10. A therapeutic acupressure device according to claim 9 wherein said clinging patches have a plurality of clinging bristles.

11. A therapeutic acupressure device according to claim 10 wherein said acupressure balls have different hardnesses.

12. A therapeutic acupressure device according to claim 11 wherein acupressure balls of different hardnesses have different colors for easy identification and selection.

13. A therapeutic acupressure device according to claim 12 wherein said cervical support is rectangular in shape and said top surface of said cervical support has a middle flat top surface portion and a downwardly sloping upper edge portion and a downwardly sloping lower edge portion.

\* \* \* \* \*